United States Patent [19]

Jeromin et al.

[11] Patent Number: 5,710,350
[45] Date of Patent: Jan. 20, 1998

[54] PROCESS FOR THE PRODUCTION OF DIGLYCEROL

[75] Inventors: Lutz Jeromin; Bernhard Gutsche, both of Hilden; Reinhard Bunte, Dormagen; Volkmar Jordan, Steinfurt, all of Germany

[73] Assignee: Henkel Kommanditgesellschaft auf Aktien, Duesseldorf, Germany

[21] Appl. No.: 522,387

[22] PCT Filed: Mar. 16, 1994

[86] PCT No.: PCT/EP94/00834

§ 371 Date: Sep. 25, 1995

§ 102(e) Date: Sep. 25, 1995

[87] PCT Pub. No.: WO94/21582

PCT Pub. Date: Sep. 29, 1994

[30] Foreign Application Priority Data

Mar. 25, 1993 [DE] Germany ............ 43 09 741.3

[51] Int. Cl.$^6$ ............................................. C07C 31/18
[52] U.S. Cl. .............................. 568/869; 568/868; 568/870
[58] Field of Search ............................. 568/870, 869, 568/868

[56] References Cited

U.S. PATENT DOCUMENTS 2,487,208  11/1949  Alsop ........................ 260/615

FOREIGN PATENT DOCUMENTS 3410520  9/1985  Germany.
4124665  1/1993  Germany.

OTHER PUBLICATIONS

Minner et al., Glycerol, Reinhold publ. Corp., New York 1953, pp. 366 to 368.
Chemical Abstracts, vol. 98, no 21, 23 May 1983, abstract no. 178739j, "Diglycerol Purification", p. 600.
Chemical Abstracts, vol. 113, No. 15, 8 Oct. 1990, Colombus, Ohio, US; abstract No. 132708y, I. Naribayasi et al'Preparation of High–Purity Diglycerin, p 708 ; col. 1 ; & JP .A.02 169 536 (Sakamoto Yakuhin).
Chemical Abstracts, vol. 98, No. 21, 23 May 1983, Columbus, Ohio, US; abstract No. 178739j, 'Diglycerol Purification', p. 600 ;col. 1; see abstract & JP .A.57 203 023 (Daicel Chemical Industries).
Milner and Dalton, Glycerol, Reinhold Publ. Corp. New York 1953, pp. 366 to 368.
G. Jakobson, Fette–Seifen–Anstrichmittel 3(88) 1986, pp. 101 to 106.

*Primary Examiner*—Marianne M. Cintins
*Assistant Examiner*—Dwayne C. Jones
*Attorney, Agent, or Firm*—Ernest G. Szoke; Wayne C. Jaeschke; Daniel S. Ortiz

[57] ABSTRACT

A process for preparing diglycerol in high concentrations and high yields by partially reacting glycerol in the presence of an alkaline catalyst to form a reaction mixture containing from 10 to 15% by weight of diglycerol and separating the unreacted glycerol from the reaction mixture in a wiped film or short path first distillation zone at a reduced pressure of 0.5 to 5 mbar and distilling a bottoms product from the first distillation zone in a second distillation zone which is a short path distillation zone at a pressure of 0.05 to 0.3 mbar to obtain a second bottom product containing at least 90% by weight diglycerol. Diglycerol of higher purity can be obtained by recovering diglycerol as a distillate from a third distillation zone.

20 Claims, 1 Drawing Sheet

PROCESS FOR THE PRODUCTION OF DIGLYCEROL

This application is a 371 of PCT/EP94/00834, filed on Mar. 16, 1994, published as WO94/21582 Sep. 29, 1994.

FIELD OF THE INVENTION

This invention relates to a process for the production of diglycerol by condensation of glycerol in the presence of a basic catalyst, preferably sodium or potassium hydroxide, at reaction temperatures of 200° to 275° C. and, more particularly, at reaction temperatures of 220° to 240° C. and subsequent concentration of the diglycerol by distillation.

RELATED ART

Diglycerol and higher oligomers of glycerol, such as tri- and tetraglycerol, which are also known generally as polyglycerols, are normally obtained in the alkali-catalyzed condensation of glycerol at elevated temperature. These ethers have relative molecular weights of 166 (6 carbon atoms) to 2,238 (90 carbon atoms) and contain 4 to 32 hydroxyl groups. The polyglycerols are prepared not only by the base-catalyzed dehydration of glycerol, but also by purification of the polyglycerol-containing distillation residue emanating from the synthetic production of glycerol via epichlorohydrin (DE 34 10 520 A1). Their purification is carried out in one or more cation exchangers and an anion exchanger by evaporation of water and vacuum distillation.

For the industrial production of polyglycerol by condensation of glycerol, glycerol is heated together with an alkaline catalyst at a temperature of 200° to 275° C. under normal pressure or reduced pressure. Sodium hydroxide or sodium acetate is normally used as the catalyst. In a typical process, approximately 0.3% of sodium hydroxide is added to glycerol and the reaction mixture is heated to a temperature of around 230° C. at which the water begins to distil off. The mixture is then slowly heated to 260°–265° C. and kept at that temperature until the calculated quantity of water has distilled off. The time required for removal of the water changes slightly with the reaction conditions, although a reaction time of 11 hours for the production of diglycerol is typical. The reaction product obtained contains a number of different polyglycerols and also unreacted glycerol. It is called diglycerol, triglycerol, etc. according to its average composition which is characterized by the hydroxyl value or the quantity of water distilled off (book: Miner and Dalton, Glycerol, Reinhold Publ. Corp. New York 1953, pages 366 to 368).

It is also known that the polyglycerols present in the reaction mixture can be separated by acetylation and distillation of the acetates. Another method of separating the polyglycerols comprises distilling their allyl ethers or their isopropylidene derivatives. The polyglycerols are obtained by hydrolysis. It is also known that the lower polyglycerols can be directly separated by distillation providing a sufficiently low pressure (vacuum) is applied.

Subsequent separation of the reaction mixture into the individual polyglycerols is not possible in the production of diglycerol by autocondensation of glycerol. Although there is no need for subsequent separation in certain known production processes (G. Jakobson, Fette-Seifen-Anstrichmittel 3(88) 1986, pages 101 to 106) these processes are attended by the disadvantage that either the starting substances are difficult to obtain or the synthesis involves several intermediate stages.

In another known process for the production of polyglycerols by autocondensation of glycerol, glycerol is condensed in the presence of lithium hydroxide at temperatures of 200° to 300° C. and, more particularly, at 260° C. The water of reaction is continuously distilled. Where a high glycerol content is required, the condensation reaction is terminated when the quantity of water theoretically required for the formation of diglycerol has been separated. The diglycerol may then be separated from the oligoglycerol mixture formed by distillation in a high vacuum (DE 41 24 665 A1).

The polyglycerols, including in particular diglycerol, are used as starting materials for esterification and transesterification reactions with fatty acid and fatty acid esters. The esters of polyglycerols and of diglycerol offer an even greater range of variation in their properties than the simple glycerides and, accordingly, are used for a number of applications of which only two are to be mentioned. They are suitable as raw materials for the production of polymers, being incorporated for example in alkyd resins by condensation via the hydroxyl groups and representing polycondensation units of the type used in particular for the development of polyurethane foams (DE 41 24 665 A1). By virtue of its lipophilic and hydrophilic properties, esters of diglycerol are also widely used as an emulsifier in the cosmetics and food industry.

The problem addressed by the present invention was to enable diglycerol to be economically produced in concentrations of more than 90% without significant losses of starting material, glycerol condensed in the presence of a basic catalyst being used as the starting material.

BRIEF DESCRIPTION OF THE INVENTION

According to the invention, the solution to this problem is characterized in that the reaction is only carried out to a partial conversion of 10 to 15% by weight of diglycerol in the reaction mixture and is terminated by cooling the reaction mixture to temperatures below 200° C. In a first distillation stage, the reaction mixture is distilled in a wiped-film evaporator or short-path evaporator under a pressure of 0.5 to 5 mbar, more particularly under a pressure of 1 to 2 mbar, and at a bottom temperature of 125° to 170° C., more particularly at a bottom temperature of 130° to 140° C. Wiped-film evaporators are evaporators in which a highly viscous, high-boiling mixture is applied to a heated wall on which it is mechanically distributed by rotating wiping elements. Thin continuous liquid layers or rather liquid films are thus formed. The film surfaces are continuously renewed so that local overheating is avoided. The vapors formed flow against the flow of product film and leave the evaporator in the externally arranged condenser. Wiped-film evaporators are generally operated under pressures of only a few mbar and the residence time for the product is only a few seconds.

The short-path evaporator mentioned, which is also known as a molecular evaporator, is suitable for the distillation of even more highly boiling and temperature-sensitive products. Through a condenser built into the evaporator, it provides for operating or boiling pressures in the fine and high vacuum range (1 to $10^{-3}$ mbar or $10^{-3}$ to $10^{-5}$ mbar).

After passing through the first distillation stage, the sump from the first distillation stage is distilled in a second, following distillation stage comprising a short path evaporator under a pressure of 0.05 to 0.3 mbar and, more particularly, under a pressure of 0.1 to 0.2 mbar and at a bottom temperature of 140° to 170° C. and, more particularly, at a bottom temperature of 145° to 155° C. so that a bottom product containing more than 90% by weight of diglycerol is obtained in this second distillation stage.

Accordingly, the problem addressed by the present invention is solved by a coordinated combination of reaction management and product separation. The production of higher oligomers of glycerol, namely triglycerol, tetraglycerol, etc., is avoided by the special control of the reaction. It is consciously accepted that the reaction mixture has a relatively low content of diglycerol by comparison with known processes. This disadvantage is obviated by the following two distillation stages so that a diglycerol with a content of more than 90% is obtained as the end product. The problems of known processes, namely that both glycerol and higher oligomers of glycerol have to be removed to increase the diglycerol content and that, in addition, the formation of these higher oligomers affects the economy of the process, do not arise in the process according to the invention because the formation of the higher oligomers is avoided.

The process may be carried out both discontinuously and continuously. In one preferred embodiment of the invention, the reaction is carried out continuously in a tube reactor. The catalyst (for example NaOH) is introduced in the form of a solution.

BRIEF DESCRIPTION OF THE DRAWINGS

The FIGURE is a schematic representation of the process.

DETAIL DESCRIPTION OF THE INVENTION

Figure 1:
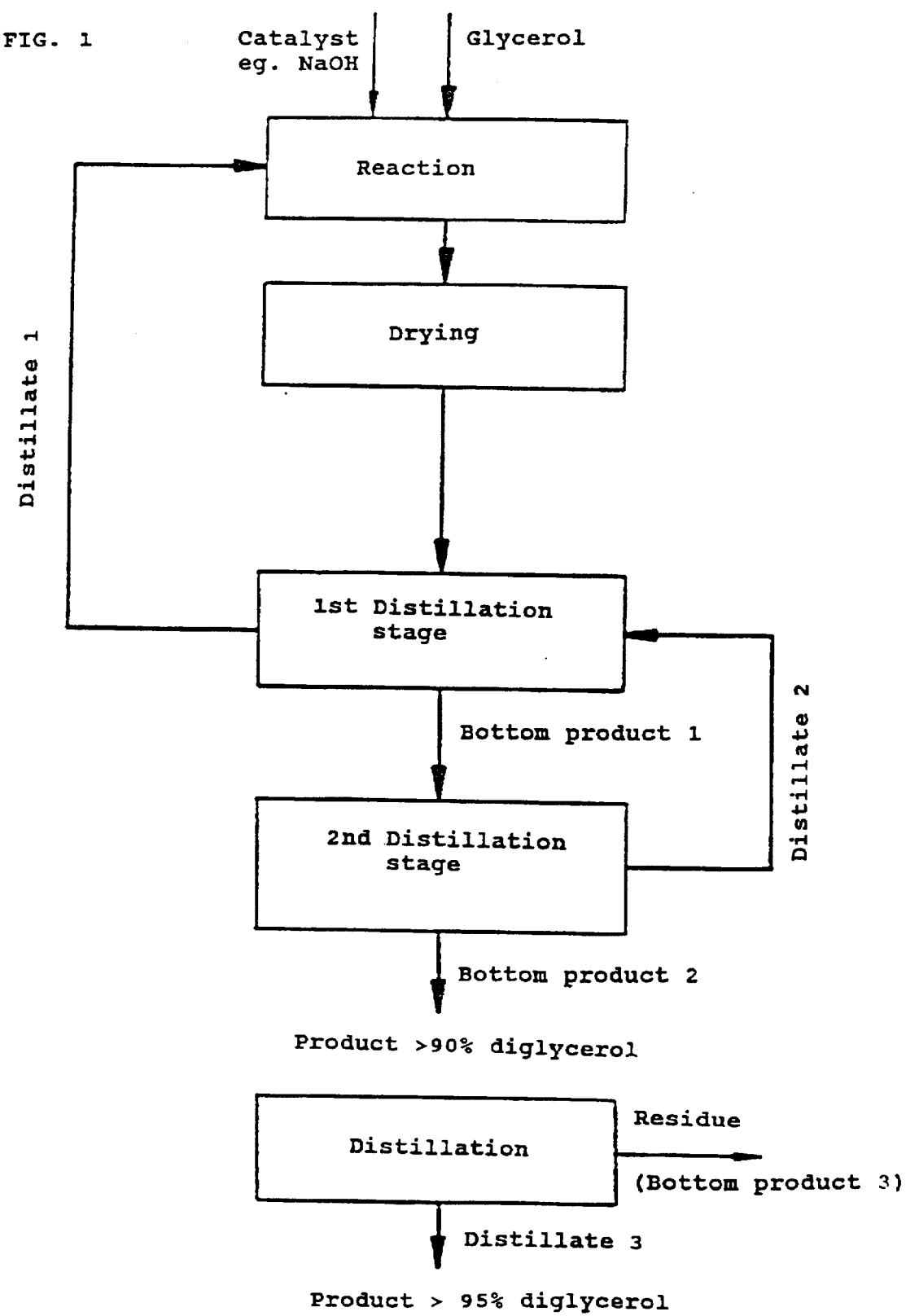

In the continuous embodiment, it is of advantage to ensure that no back mixing occurs in the reactor. Accordingly, it is proposed that the tube reactor should contain inert packings to suppress circulation flows, particularly where it is of relatively large diameter, for example more than 0.3 m in diameter. Alternatively to the homogeneously dissolved catalyst, it is also possible to use a catalyst-containing fixed bed. The fixed-bed catalyst may be, for example, an NaX zeolite, more particularly Wessalith P (a product of Henkel KGaA). In addition, it is of advantage in the continuous embodiment to dry the reaction mixture formed after the reaction, i.e. to remove the water of reaction, before the reaction mixture is subjected to the first distillation stage. In the discontinuous embodiment, a large part of the water of reaction is distilled off during the actual reaction.

The process according to the invention may also be carried out discontinuously by replacing the tube reactor with a stirred tank reactor.

The process is characterized in that, for the most part, only diglycerol, water of reaction and unreacted glycerol are formed. It is of advantage to return the distillate of the first distillation stage, which consists of substantially pure glycerol, to the reaction stage. However, this distillate may also be used as a starting substance in other processes. However, recycling to the reaction stage is particularly advantageous because, in this case, it is mainly only water of reaction and pure diglycerol that are formed over the process as a whole. Product losses are minimal.

In order further to reduce product losses, it is of advantage to mix the distillate of the second distillation stage, which contains glycerol and diglycerol, with the feed of the first distillation stage and, in this way, to return it to the first distillation stage.

The bottom product of the second distillation stage has a diglycerol content of more than 90% and a negligible glycerol content. In another advantageous embodiment of the process according to the invention, the purity of the product can be increased by distilling the bottom product of the second distillation stage in a short-path evaporator under a pressure of at most 0.05 mbar and at a temperature of 185° to 215° C. in a third distillation stage to obtain a distillate containing more than 95% by weight of diglycerol. This fine distillation not only increases the diglycerol content, it also removes salts from the product and decolors the product.

Embodiments of the invention are described in the following.

The invention with its key features and most important advantageous embodiments is illustrated in the form of a flow chart in FIG. 1. After addition of the catalyst (sodium hydroxide) and glycerol, the condensation reaction is carried out to a partial conversion of 10 to 15% by weight. The reaction is terminated by cooling and, in the case of the continuous process, the reaction mixture is dried. The distillate 1 consisting almost solely of glycerol obtained in the following first distillation stage is returned to the reaction stage. The bottom product 1 obtained is separated into a distillate 2 and a bottom product 2 in a second distillation stage. The distillate 2 is returned to the first distillation stage. The bottom product 2 contains more than 90% of diglycerol and, in many cases, is the required end product. In other cases where an even higher diglycerol content is required, the bottom product 2 is separated into a distillate containing more than 95% of diglycerol and a residue (bottom product 3) in a third distillation stage.

EXAMPLE 1

(Discontinuous Reaction)

Glycerol was reacted with the catalyst NaOH (used in a quantity of 0.5% by weight, based on the glycerol) in a stirred reactor at a temperature of 230° C.

After a reaction time of 8 hours, the diglycerol content is 12.5% by weight. The triglycerol content is 1%. The percentage content of higher oligoglycerols is below the detection limit of 0.1% by weight.

EXAMPLE 2

(Continuous Reaction)

Glycerol was reacted with the catalyst NaOH (used in a quantity of 0.35% by weight, based on glycerol) at 240° C. in a tube reactor which was filled with inert packings to suppress back-mixing effects.

A diglycerol content of 12% by weight was obtained; the triglycerol content was 0.8% by weight. Higher oligoglycerols could not be detected (<0.1% by weight).

EXAMPLE 3

(Continuous Reaction, Heterogeneous Catalysis)

Glycerol was reacted at 240° C. in a fixed-bed reactor filled with an NaX catalyst (zeolite of the Wessalith P type). A diglycerol content of 12.5% and a content of higher glycerols of 0.9% were obtained.

EXAMPLE 4

(Two-Stage Distillation)

The reaction mixture of Example 1 was distilled in two stages.

The first distillation stage was carried out in a short-path evaporator under a pressure of 1.2 mbar and at a temperature of 140° C. The second distillation stage was also carried out in a short-path evaporator, but under a pressure of 0.1 mbar and at a temperature of 155° C. The distillate of the second stage was continuously returned to the first distillation stage. The following concentrations were obtained:

|  | Distillate | Bottom product |
|---|---|---|
| 1st Stage | <0.5% by weight diglycerol | 30–40% by weight diglycerol |
| 2nd stage | 15% by weight diglycerol | 90–91.5% by weight diglycerol |

EXAMPLE 5
(3rd Distillation Stage)

The distillation product (bottom product of the 2nd stage) of Example 4 was distilled in a short-path evaporator at a temperature of 205° C. and under a pressure of $10^{-2}$ mbar. The distillate was 98% salt-free diglycerol.

The loss (bottom product of the 3rd stage) in the form of residue (salt and polyglycerol) amounted to 25% by weight.

We claim:

1. A process for the production of diglycerol by condensation of glycerol in the presence of a basic catalyst, at a reaction temperature of from 200° C. to 275° C. and concentration of the diglycerol by distillation, which comprises:
   a) partially reacting glycerol, in a reaction zone, to form a reaction mixture containing 10% to 15% by weight of diglycerol;
   b) terminating the reaction by cooling the reaction mixture to a temperature below 200° C.;
   c) distilling the reaction mixture in a first distillation zone which comprises a distillation zone selected from the group consisting of a wiped film evaporator zone and a short-path evaporator zone, at a pressure of 0.5 to 5 mbar and a bottom temperature of the distillation zone of 125° C. to 170° C. to form a first bottom product; and
   d) distilling the first bottom product in a second distillation zone comprising a short path evaporator zone at a pressure of 0.05 to 0.3 mbar and a bottom temperature of 140° C. to 170° C. to obtain a second bottom product containing more than 90% by weight of diglycerol.

2. The process as claimed in claim 1, wherein the reaction is carried out continuously in a tube reactor containing a fixed bed of catalyst.

3. The process as claimed in claim 1 wherein the reaction is carried out continuously in a tube reactor containing inert packing elements.

4. The process as claimed in claim 2 wherein the reaction mixture is dried before distillation in the first distillation zone.

5. The process as claimed in claim 1, wherein the reaction is carried out in a stirred tank reactor.

6. The process as claimed in claim 1 wherein a distillate from the first distillation zone is returned to the reaction zone.

7. The process as claimed in claim 1 wherein a distillate from the second distillation zone is returned to the first distillation zone.

8. The process as claimed in claim 1 wherein the second bottom product from the second distillation zone is distilled in a third distillation zone comprising a short-path evaporator under a pressure not higher than 0.05 mbar and a temperature of 185° C. to 215° C. to obtain a distillate containing more than 95% by weight of diglycerol.

9. The process of claim 1 wherein the pressure in the first distillation zone is from 1 to 2 mbar.

10. The process of claim 1 wherein the bottom temperature in the first distillation zone is from 130° C. to 140° C.

11. The process of claim 1 wherein the reaction temperature is from 220° C. to 240° C.

12. The process of claim 1 wherein the catalyst comprises at least one member selected from the group consisting of sodium hydroxide and potassium hydroxide.

13. The process of claim 1 wherein the pressure in the second distillation zone is from 0.1 to 0.2 mbar.

14. The process of claim 1 wherein the first distillation zone comprises a wiped film evaporator.

15. The process of claim 3 wherein the reaction mixture is dried before distillation in the first distillation zone.

16. The process of claim 2 wherein a distillate from the first distillation zone is returned to the reaction zone.

17. The process of claim 3 wherein a distillate from the first distillation zone is returned to the reaction zone.

18. The process of claim 2 wherein a distillate from the second distillation zone is returned to the first distillation zone.

19. The process of claim 3 wherein a distillate from the second distillation zone is returned to the first distillation zone.

20. The process of claim 2 wherein the second bottom product is distilled in a third distillation zone comprising a short path evaporator at a pressure not higher than 0.05 mbar and a temperature of 185° C. to 215° C. to obtain a distillate containing more than 95% by weight of diglycerol.

* * * * *